United States Patent [19]

Miura et al.

[11] Patent Number: 5,574,152
[45] Date of Patent: Nov. 12, 1996

[54] 4-(1,1-DIALKOXYCARBONYLALKYL) AZETIDIN-2-ONE DERIVATIVE AND PROCESS FOR PRODUCING 4-(1-CARBOXYALKYL) AZETIDIN-2-ONE DERIVATIVE USING THE SAME

[75] Inventors: Takashi Miura; Toshiyuki Murayama; Akifumi Yoshida; Toyohiko Kobayashi, all of Tokyo, Japan

[73] Assignee: Takasago International Corporation, Tokyo, Japan

[21] Appl. No.: 277,319

[22] Filed: Jul. 25, 1994

Related U.S. Application Data

[62] Division of Ser. No. 987,779, Dec. 9, 1992, Pat. No. 5,371,214.

[30] Foreign Application Priority Data

Dec. 9, 1991 [JP] Japan .................................. 3-324737
Dec. 20, 1991 [JP] Japan .................................. 3-338673

[51] Int. Cl.$^6$ ............................ C07D 705/08; C07B 37/06
[52] U.S. Cl. ............................................................ 540/200
[58] Field of Search ............................................. 540/200

[56] References Cited

FOREIGN PATENT DOCUMENTS

| 0045198 | 2/1982 | European Pat. Off. . |
| 0052299 | 5/1982 | European Pat. Off. . |
| 0071908 | 9/1989 | European Pat. Off. . |

OTHER PUBLICATIONS

C. U. Kim et al., *Tetrahedron Lett.*, 28 (5) 507–510 (1987).
T. Chiba et al., *Chem. Lett.*, 1343–1346 (1985).
T. Shibata et al., *Tetrahedron Lett.*, 26 (39) 4739–4742 (1985).
Y. Nagao et al., *J. Am. Chem. Soc.*, 108, 4673–4675 (1986).
Y. Nagao, Chem Abs 108, 5705s (1987).
L. M. Fuentes et al., *J. Am. Chem. Soc.*, 108, 4675–4676 (1986).
R. Dèziel et al., *Tetrahedron Lett.*, 27 (47) 5687–5690 (1986).
Y. Ito et al., *Tetrahedron Lett.*, 28 (52) 6625–6628 (1987).
M. Endo, *Can. J. Chem.*, 65, 2140–2145 (1987).
A. Martel et al., *Can. J. Chem.*, 66, 1537–1539 (1988).
D. H. Shih et al., *Heterocycles*, 21 (1) 29–40 (1984).

Pearson, J Org Chem 52, 3176 (1987).
T. Iimori et al., *Tetrahedron Lett.*, 27 (19) 2149–2152 (1986).
Y. Ito et al., *Yuki Gosei Kagaku Kyokaishi*, 47 (7) 606–618 (1985).
R. Joyeau et al., *J. Chem. Soc.*, Perkin Trans. I, 1899–1907 (1987).
R. Joyeau et al., *Tetrahedron Lett.*, 30 (3) 337–340 (1989).
J. Tsuji et al., *Tetrahedron Lett.*, (7) 613–616 (1979).
T. Mandai et al., *J. Org. Chem.*, 54 5395–5397 (1989).
C. W. Greengrass et al. *Tetrahedron Letters.*, vol. 22, No. 52, pp. 5335–5338 (1981).
Nagao, Kagaku 42, 190–196 (1987).
Zto, Chem Abs 112, 55296 (1989).
Choi et al Let. Letters 35, 2275 (1994).

*Primary Examiner*—Mark L. Berch
*Attorney, Agent, or Firm*—Sughrue, Mion, Zinn, Macpeak & Seas

[57] ABSTRACT

A process for preferentially producing a 4-(1-carboxyalkyl) azetidin-2-one derivative represented by formula (IIβ):

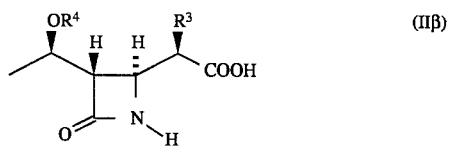

(IIβ)

wherein $R^3$ represents a lower alkyl group and $R^4$ represents a hydrogen atom or a hydroxy-protective group, which involves deesterifying and decarboxylating a 4-(1,1-dialkoxycarbonylalkyl) azetidin-2-one derivative represented by formula (I):

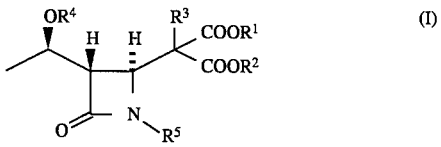

(I)

wherein $R^1$ and $R^2$ are identical or different and each represents an alkyl group, an alkenyl group, or an aralkyl group, $R^3$ and $R^4$ each has the meaning as defined above, and $R^5$ represents an amino-protective group, and after that, eliminating the amino-protective group from the derivative, where the 4-(1-carboxyalkyl)azetidin-2-one derivative of formula (IIβ) is present in an amount of at least 61% by mol of all 4-(1-carboxyalkyl)azetidin-2-one derivatives produced.

2 Claims, No Drawings

4-(1,1-DIALKOXYCARBONYLALKYL) AZETIDIN-2-ONE DERIVATIVE AND PROCESS FOR PRODUCING 4-(1-CARBOXYALKYL) AZETIDIN-2-ONE DERIVATIVE USING THE SAME

This is a divisional of application Ser. No. 07/987,779 filed Dec. 9, 1992 now U.S. Pat. No. 5,371,214.

FIELD OF THE INVENTION

The present invention relates to a novel 4-(1,1-dialkoxycarbonylalkyl)azetidin-2-one derivative and a process for producing, from the derivative, a 4-(1-carboxyalkyl)azetidin-2-one derivative which is useful as an intermediate for various 1β-alkylcarbapenem-type antibacterial agents.

BACKGROUND OF THE INVENTION

Carbapenem-type antibacterial agents are excellent antibacterials having strong antibacterial activity against a wide spectrum of bacteria ranging from gram-positive bacteria to gram-negative bacteria including *Pseudomonas aeruginosa*. Hence, new antibacterials of the carbapenem-type are being energetically developed in recent years. Although carbapenem derivatives having no substituent at the 1-position in the carbapenem backbone, such as thienamycin shown by formula (III):

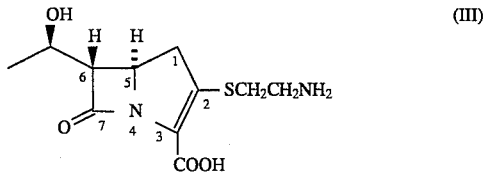

have drawbacks that they are chemically unstable at high concentrations and that they are readily metabolized by dehydropeptidase I, incorporation of a β-configuration alkyl group at the 1-position improves the stability of such carbapenem derivatives and enables the derivatives to be used alone without the necessity of addition of a dehydropeptidase inhibitor thereto. Therefore, efforts are currently being made to develop 1β-alkylcarbapenem-type antibacterials and also to develop methods of synthesizing 4-[(R)-1-carboxyalkyl]azetidin-2-one derivatives represented by formula (IIβ):

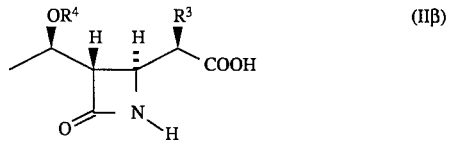

(wherein $R^3$ represents a lower alkyl group and $R^4$ represents a hydrogen atom or a hydroxyl-protective group), which derivatives can be used as intermediates for such antibacterials.

As synthetic methods for compounds (IIβ) described above, many reports have been made. The most promising method of these is to alkylate a 4-acetoxyazetidin-2-one derivative represented by formula (IV):

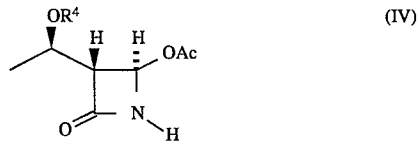

(wherein $R^4$ has the meaning as defined above and Ac denotes an acetyl group) at the 4-position with any of various nucleophilic agents thereby to incorporate a side chain. With respect to this method, the following reports, for example, have been made: alkylation with a propionic acid ester enolate [C. U. Kim et al., *Tetrahedron Lett.*, 28 (5) 507–510 (1987); T. Chiba et al., *Chem. Lett.*, 1343–1346 (1985); and T. Shibata et al., *Tetrahedron Lett.*, 26 (39) 4739–4742 (1985)]; alkylation with a propionimide enolate [Y. Nagao et al., *J. Am. Chem. Soc.*, 108, 4673–4675 (1986); Yoshimitsu Nagao, *Kagaku (Chemistry)*, 42 (3) 190–196 (1987); L. M. Fuentes et al., *J. Am. Chem. Soc.*, 108, 4675–4676 (1986); R. Deziel et al., *Tetrahedron Lett.*, 27 (47) 5687–5690 (1986); and Y. Ito et al., *Tetrahedron Lett.*, 28 (52) 6625–6628 (1987)]; and alkylation with a propionic acid thiol ester enolate [M. Endo, *Can. J. Chem.*, 65, 2140–2145 (1987); C. U. Kim et al., *Tetrahedron Lett.*, 28 (5) 507–510 (1987); and A. Martel et al., *Can. J. Chem.*, 66, 1537–1539 (1988)].

Other methods for synthesizing compounds (IIβ) include, for example, a method of alkylating compound (V)

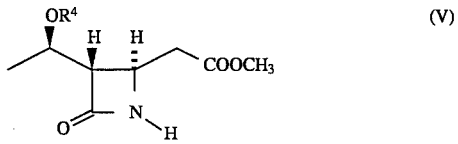

(wherein $R^4$ has the meaning as defined above) with lithium diisopropylamide [D. H. Shih et al., *Heterocycles*, 21 (1) 29–40 (1984)] and a method in which the exo-methylene group of compound (VI)

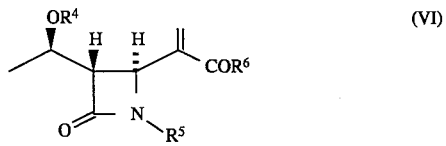

(wherein $R^4$ has the meaning as defined above, $R^5$ represents a hydrogen atom or an amino-protective group, and $R^6$ represents an alkyl group, a carboxyl group, or an alkoxycarbonyl group) is reduced by catalytic reduction or by asymmetric reduction using a specific catalyst [JP-A-58-26887 (corresponding to European Patent 71908B); C. U. Kim et al., *Tetrahedron Lett.*, 28 (5) 507–510 (1987); T. Ohta et al., *J. Org. Chem.*, 52, 3176–3178 (1987); and T. Iimori et al., *Tetrahedron Lett.*, 27 (19) 2149–2152 (1986)]. (The term "JP-A" as used herein means an "unexamined published Japanese patent application".) These methods are reported in Yoshio Itoh et al., *Yuki Gosei Kagaku (Chemistry of Organic Syntheses)*, 47 (7) 606–618, "Synthesis of the 1β-Methylcarbapenem Key Intermediates" (1989).

According to these methods, compound (IIβ) in most cases is obtained in the form of compound (II)

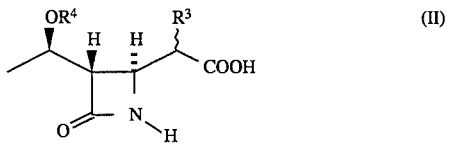

(wherein $R^3$ and $R^4$ each has the meaning as defined above) which is a mixture, in a specific proportion, of the compound (IIβ) and compound (IIα)

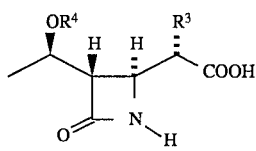

(wherein $R^3$ and $R^4$ each has the meaning as defined above) which is a stereoisomer with the compound (IIβ). This compound (IIα) having an α-configuration alkyl group can be converted to the desired compound (IIβ) having a β-configuration alkyl group by isomerization, which may be conducted by the method disclosed, for example, in D. H. Shih et al., *Heterocycles*, 21 (1) 29–40 (1984).

However, the above-described methods for synthesizing compounds (II) and (IIβ) are disadvantageous in that special and expensive reagents are used, reaction temperature is extremely low, or expensive or toxic metals are used as catalyst. Therefore, the above methods are unsuited for syntheses in large quantities and are not being practiced on an industrial scale.

Hence, there has been a desire for development of a process for efficiently producing compound (II), especially compound (IIβ) which has a β-configuration alkyl group and is more useful as an intermediate for 1β-alkylcarbapenem-type antibacterials.

SUMMARY OF THE INVENTION

Under these circumstances, the present inventors have conducted intensive studies. As a result, it has been found that a 4-(1-carboxyalkyl)azetidin-2-one derivative can be produced efficiently when it is synthesized by a method in which a 4-(1,1-dialkoxycarbonylalkyl)azetidin-2-one derivative having a structure in which a malonic acid derivative has been bonded to the azetidin-2-one backbone at the 4-position is first synthesized and this azetidin-2-one derivative is then de-esterified and decarboxylated and, in the case where an amino-protective group is present in the derivative, the protective group is eliminated. The present invention has been completed based on this finding.

Accordingly, the present invention provides a 4-(1,1-dialkoxycarbonylalkyl)azetidin-2-one derivative represented by formula (I):

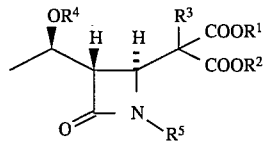

wherein $R^1$ and $R^2$ are identical or different and each represents an alkyl group, an alkenyl group, or an aralkyl group, $R^3$ represents a lower alkyl group, $R^4$ represents a hydrogen atom or a hydroxyl-protective group, and $R^5$ represents a hydrogen atom or an amino-protective group.

The present invention further provides a process for producing a 4-(1-carboxyalkyl)azetidin-2-one derivative represented by formula (II):

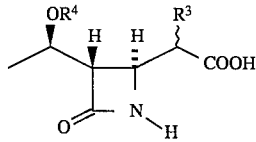

wherein $R^3$ and $R^4$ each has the meaning as defined above, which comprises de-esterifying and decarboxylating the derivative of formula (I), and in the case where an amino-protective group is present in the derivative of formula (I), eliminating the protective group from the derivative.

DETAILED DESCRIPTION OF THE INVENTION

The 4-(1,1-dialkoxycarbonylalkyl)azetidin-2-one derivative of the present invention is represented by formula (I) described above.

Examples of the alkyl group of $R^1$ and $R^2$ in the formula include straight-chain or branched alkyl groups such as methyl, ethyl, n-propyl, isopropyl, n-butyl, and tert-butyl; and monocyclic or polycyclic alkyl groups such as cyclopentyl, cyclohexyl, menthyl, fenchyl, and bornyl. Examples of the alkenyl group of $R^1$ and $R^2$ include straight-chain or branched alkenyl groups such as vinyl, allyl, 2-butenyl, and 2-methyl-2-propenyl. Examples of the aralkyl group of $R^1$ and $R^2$ include benzyl and benzhydryl. Preferably, $R^1$ and $R^2$ are identical and each represents a 2-alkenyl group.

The lower alkyl group of $R^3$ is an alkyl group having 1 to 4 carbon atoms. Examples of the lower alkyl group include methyl, ethyl, and n-propyl. Of these, a methyl group is particularly preferred.

Examples of the hydroxyl-protective group of $R^4$ include tri-substituted silyl groups such as trimethylsilyl and tert-butyldimethylsilyl; acyl groups such as acetyl; and aralkyl groups such as benzyl.

Examples of the amino-protective group of $R^5$ include tri-substituted silyl groups such as trimethylsilyl, triethylsilyl, tert-butyldimethylsilyl, and methyldiphenylsilyl; aralkyl groups which may have a substituent on the aromatic ring(s), such as benzyl, p-methoxybenzyl, p-tertbutylbenzyl, 3,4-dimethylbenzyl, phenethyl, and benzhydryl; and alkoxyalkyl groups such as tetrahydropyranyl and methoxymethyl. Of these groups, tri-substituted silyl groups are preferred.

In the case where such 4-(1,1-dialkoxycarbonylalkyl)azetidin-2-one derivatives are represented by formula (I) in which $R^5$ is a hydrogen atom (hereinafter referred to as "azetidin-2-one derivatives (Ia)"), these compounds can be produced according to, for example, the method proposed by R. Joyeau et al., *J. Chem. Soc., Perkin Trans.* I, 1899–1907 (1987); *Tetrahedron Lett.*, 30 (3) 337–340 (1989) in which a malonic acid derivative (VII) is reacted with a 4-acetoxyazetidin-2-one derivative (IV) as shown by the following scheme:

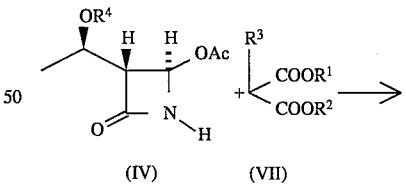

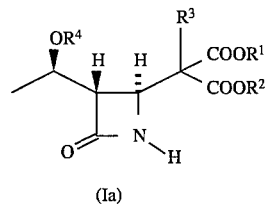

(wherein $R^1$, $R^2$, $R^3$, $R^4$, and Ac each has the meaning as defined above).

Illustratively stated, a 4-acetoxyazetidin-2-one derivative (IV) is added to a solution of a malonic acid derivative (VII) which has been activated, for example, with an alkali metal such as potassium metal, sodium metal, or lithium metal, an alkali metal hydride such as sodium hydride, an alkyl alkali metal such as butyllithium, an alkali metal alkoxide such as potassium tert-butoxide, sodium ethoxide, or sodium methoxide, an alkali metal hydroxide such as potassium hydroxide or sodium hydroxide, an alkali metal carbonate such as potassium carbonate, or the like. The reactants in the resulting mixture are then allowed to react at a temperature of from −60° to 40° C., especially preferably at room temperature (20°–30° C.), for a period of preferably from 0.5 to 15 hours, more preferably from 2 to 5 hours thereby to produce the desired compound. Examples of the solvent for use in the above method include water; alcohols such as methanol and ethanol; ethers such as diethyl ether, dioxane, and tetrahydrofuran; acetone; dimethylformamide; and mixed solvents consisting of water and one or more of such organic solvents. Of these, tetrahydrofuran is especially preferably used. The proportions of the reactant compounds are preferably such that the malonic acid derivative (VII) is used in an amount of about from 1 to 1.3 mol, particularly about 1.1 mol, per mol of the 4-acetoxyazetidin-2-one derivative (IV). The azetidin-2-one derivative (Ia) thus obtained can be purified by extraction, washing, dehydration, and so forth, which may be conducted in an ordinary way, followed by recrystallization, column chromatography, etc.

In the case where the 4-(1,1-dialkoxycarbonylalkyl)azetidin-2-one derivative of the present invention is represented by formula (I) in which $R^5$ is an amino-protective group (hereinafter referred to as "azetidin-2-one derivative (Ib)"), this compound can be produced by obtaining an azetidin-2-one derivative (Ia) in which $R^5$ is a hydrogen atom, according to the method described above, and then incorporating an amino-protective group into the derivative (Ia) by an ordinary method. For instance, a tri-substituted silyl group can be incorporated into the derivative (Ia) as the amino-protective group by reacting the derivative (Ia) with a tri-substituted silyl chloride in a solvent such as N,N-dimethylformamide, acetonitrile, or tetrahydrofuran in the presence of a base such as triethylamine, diisopropylamine, or pyridine at −20° to 30° C. for the night to a week, according to the method described in JP-A-58-26887 (corresponding to European Patent 71908B), and an aralkyl group or an alkoxyalkyl group can be incorporated by reacting the derivative (Ia) with R-X (wherein R represents an aralkyl group or an alkoxyalkyl group and X represents a halogen atom) in the above solvent in the presence of an alkali such as potassium hydroxide, sodium hydroxide, or sodium hydride at 0° to 30° C. for 3 to 24 hours, according to the method proposed by D. Reuschling et al., *Tetrahedron Lett.*, (7) 615–618 (1978).

Further, according to the present invention, compound (I) thus obtained is de-esterified and decarboxylated by an ordinary method, whereby a 4-(1-carboxyalkyl)azetidin-2-one derivative (II) can be obtained.

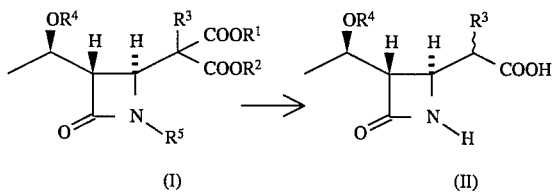

(wherein $R^1$, $R^2$, $R^3$, $R^4$, and $R^5$ each has the meaning as defined above.)

The de-esterification and decarboxylation reactions can, for example, be performed by hydrolysis and heating in an ordinary way. Illustratively stated, compound (I) is hydrolyzed in the presence of a base, such as sodium hydroxide, potassium hydroxide, or lithium hydroxide, and the hydrolyzate is then decarboxylated by heating it to 80° to 120° C. In the case where $R^1$ and $R^2$ are an aralkyl group, the de-esterification may also be accomplished by hydrogenation which is conducted using palladium carbon in the presence of an amine.

In the case where compound to be used as a raw material is represented by formula (I) in which $R^1$ and $R^2$ are a 2-alkenyl group, it is possible to carry out the de-esterification and decarboxylation reactions by the method described above. However, it is preferable that the de-esterification and decarboxylation reactions of such compound (I) be performed by reacting formic acid or an amine salt of formic acid with the compound (I) in the presence of a palladium compound; this is an application of, for example, the method proposed by J. Tsuji et al., *Tetrahedron Lett.*, (7) 613–616 (1979). This method is preferred in that both de-esterification and decarboxylation can be carried out in a single step. As the palladium compound for use in the above method, any palladium compound may be employed as long as it is capable of generating zerovalent palladium, which is an active species, in the reaction system. Examples of such palladium compounds include divalent palladium compounds such as palladium acetate, palladium chloride, and palladium acetylacetonate; and zerovalent palladium compounds such as tribenzylidenedipalladium and tetrakis(triphenylphosphine)palladium. Along with the divalent palladium compound described above, a trialkylphosphine such as triethylphosphine or tributylphosphine, a triarylphosphine such as triphenylphosphine or tritolylphosphine, or the like is used as a compound to be a ligand. Due to the presence of both the palladium compound and the ligand compound, a complex is formed in the reaction system and functions as a catalyst to accelerate the reaction. This reaction may be conducted using a solvent, e.g., an ether such as 1,4-dioxane or tetrahydrofuran, toluene, or benzene, by heating the reaction mixture with refluxing for from 1 to 5 hours. The proportions of the reactant compounds preferably are such that the amount of the palladium compound is about from 0.01 to 0.1 mol and the amount of formic acid or a formic acid amine salt is about from 3 to 15 mol, per mol of the azetidin-2-one (I).

In the case where the raw compound is azetidin-2-one derivatives (Ia) represented by formula (I) in which $R^5$ is a hydrogen atom, the de-esterification and decarboxylation reactions of these compounds selectively yield α-alkyl isomers (IIα) as compounds (II). Although the configuration for the alkyl group at the 1-position in the carbapenem backbone of each of the final desired compounds is β-configuration, the α-alkyl isomers (IIα) obtained can be converted to β-alkyl isomers (IIβ) by isomerizing the α-alkyl isomers according to the known method described above.

On the other hand, in the case where the raw compound is azetidin-2-one derivatives (Ib) represented by formula (I) in which $R^5$ is an amino-protective group, the desired compound (II) can be obtained by conducting the de-esterification and decarboxylation reactions as described above and then eliminating the amino-protective group. This process is preferred because β-alkyl isomer (IIβ) is preferentially obtained as compound (II) and is, hence, of high value in industrial utilization thereof. The elimination reaction for the amino-protective group is conducted in different ways according to the kind of the protective group. For example, in the case where the protective group is a tri-substituted silyl group, the elimination may be accomplished by reacting an acid such as diluted hydrochloric acid or tetrabutylammonium fluoride. In the case where the protective group is benzyl, phenethyl, or benzhydryl group or the like which may have a substituent, the elimination may be carried out by reacting the de-esterified and decarboxylated compound with sodium metal in liquid ammonia by means of Birch's reduction.

According to the present invention, a 4-(1-carboxyalkyl)azetidin-2-one derivative useful as an intermediate for 1β-alkylcarbapenem-type antibacterials can be produced efficiently.

The present invention will be explained below in more detail with reference to Examples, but the present invention is not construed as being limited thereto.

For the following measurements, the instruments specified below were used.

Melting point:
Type MP-S3 (manufactured by Yanagimoto Shoji K.K., Japan)

Mass spectrum (MS):
M-80B mass spectrometer (ionization potential: 20 eV) (manufactured by Hitachi Ltd., Japan)

Infrared absorption spectrum (IR):
Type IR-810 (manufactured by JASCO Inc., Japan)

$^1$H Nuclear magnetic resonance spectrum ($^1$H-NMR):
Type AM-400 (400 MHz) (manufactured by Bruker Inc.)
Internal standard: tetramethylsilane

EXAMPLE 1

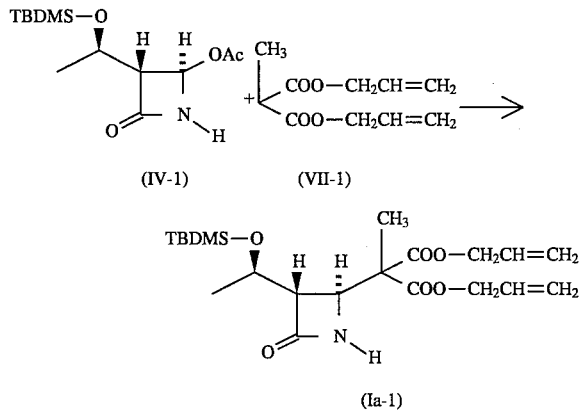

(In the above scheme, Ac has the meaning as defined hereinabove and TBDMS denotes a tert-butyldimethylsilyl group. The same applies hereinafter.)

In 50 ml of tetrahydrofuran was suspended 2.52 g (62.9 mmol) of 60% sodium hydride. While this suspension was kept being stirred at room temperature, a solution prepared by dissolving 11.88 g (60.0 mmol) of diallyl methylmalonate (VII-1) in 20 ml of tetrahydrofuran was added thereto dropwise over a period of 20 minutes. After the resulting mixture was further stirred for 2.5 hours, a solution prepared by dissolving 14.35 g (50.0 mmol) of a 4-acetoxyazetidin-2-one derivative (IV-1) in 30 ml of tetrahydrofuran was added thereto dropwise over a period of 15 minutes, and a reaction was allowed to proceed at room temperature for 15 hours.

To the reaction mixture was added 30 ml of a saturated aqueous solution of ammonium chloride. After stirring and liquid separation, the tetrahydrofuran layer obtained was washed with saturated aqueous common salt solution and dehydrated with anhydrous magnesium sulfate. Subsequently, the solvent was removed by distillation to obtain 23.5 g of crude crystals. This crude product was then recrystallized using hexane, thereby obtaining 18.03 g (percent yield 85%) of an azetidin-2-one derivative (Ia-1) as white crystals.

Melting point: 82°–82.5° C. MS (m/e): 426 (M$^+$+1), 410, 368 IR (KBr) cm$^{-1}$: 1765, 1735 $^1$H-NMR (CDCl$_3$) δ ppm: 0.07 (s, 6H), 0.88 (s, 9H), 1.14 (d, J=6.3 Hz, 3H), 1.50 (s, 3H), 3.03 (m, 1H), 4.19 (d, J=2–1 Hz, 1H), 4.21 (m, 1H), 4.64 (m, 4H), 5.27 (m, 2H), 5.34 (m, 2H), 5.88 (m, 2H), 5.96 (broad s, 1H)

EXAMPLE 2

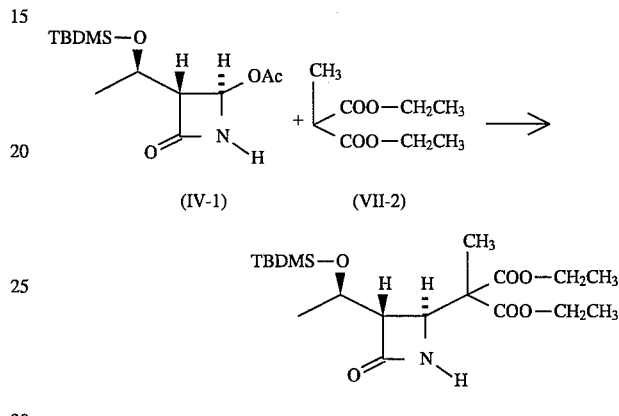

Five ml of hexane was added to 1.12 g (28.0 mmol) of 60% sodium hydride, subsequently the resulting mixture was stirred, and the hexane was then removed by decantation. This procedure was repeated several times to wash the sodium hydride. Thereafter, 20 ml of tetrahydrofuran was added to the sodium hydride. While this mixture was kept being stirred at room temperature, a solution prepared by dissolving 4.52 g (26.0 mmol) of diethyl methylmalonate (VII-2) in 20 ml of tetrahydrofuran was added thereto dropwise over a period of 15 minutes. After the resulting mixture was further stirred for 30 minutes, a solution prepared by dissolving 5.74 g (20.0 mmol) of a 4-acetoxyazetidin-2-one derivative (IV-1) in 20 ml of tetrahydrofuran was added thereto dropwise over a period of 10 minutes, and a reaction was allowed to proceed at room temperature for 1 hour.

To the reaction mixture was added 25 ml of a saturated aqueous solution of ammonium chloride. After stirring and liquid separation, the tetrahydrofuran layer obtained was washed with saturated aqueous common salt solution and dehydrated with anhydrous magnesium sulfate. Subsequently, the solvent was removed by distillation to obtain crude crystals. This crude product was then recrystallized using hexane, thereby obtaining 6.17 g (percent yield 77%) of an azetidin-2-one derivative (Ia-2) as white crystals.

Melting point: 100.5°–101° C. MS (m/e): 402 (M$^+$+1), 386, 344 IR (KBr) cm$^{-1}$: 1770, 1735 $^1$H-NMR (CDCl$_3$) δ ppm: 0.07 (s, 6H), 0.88 (s, 9H), 1.14 (d, J=6.3 Hz, 3H), 1.26, 1.28 (2 overlapping t, J=7.1Hz, 6H), 1.46 (s, 3H), 3.01 (m, 1H), 4.15 (d, J=2.2 Hz, 1H), 4.21 (m, 5H), 5.98 (broad s, 1H)

EXAMPLE 3

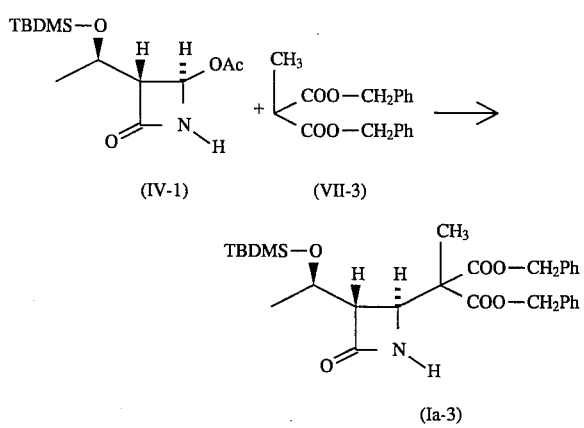

(In the above scheme, Ph denotes a phenyl group. The same applies hereinafter.)

In 5 ml of tetrahydrofuran was suspended 0.43 g (10.8 mmol) of 60% sodium hydride. While this suspension was kept being stirred at room temperature, a solution prepared by dissolving 3.13 g (10.5 mmol) of dibenzyl methylmalonate (VII-3) in 3 ml of tetrahydrofuran was added thereto dropwise over a period of 20 minutes. After the resulting mixture was further stirred at room temperature for 30 minutes, a solution prepared by dissolving 2.87 g (10.0 mmol) of a 4-acetoxyazetidin-2-one derivative (IV-1) in 5 ml of tetrahydrofuran was added thereto dropwise over a period of 15 minutes, and a reaction was allowed to proceed at room temperature for 1.5 hours.

To the reaction mixture was added 15 ml of a saturated aqueous solution of ammonium chloride. After stirring, extraction was conducted using 20 ml of ethyl acetate. The ethyl acetate layer obtained was washed with water, subsequently dehydrated with anhydrous magnesium sulfate, and then concentrated, thereby to obtain an oily substance. This oily substance was purified by silica gel column chromatography (developing solvent; hexane:ethyl acetate=4:1 by volume), thereby obtaining 4.28 g (percent yield 82%) of an azetidin-2-one derivative (Ia-3) as white crystals.

Melting point: 93°–93.5° C. MS (m/e): 526 (M$^+$+1), 510, 468 IR (KBr) cm$^{-1}$: 1770, 1735 $^1$H-NMR (CDCl$_3$) δ ppm: 0.06 (s, 6H), 0.87 (s, 9H), 1.09 (d, J=6.4 Hz, 3H), 1.50 (s, 3H), 3.03 (m, 1H), 4.19 (m, 1H), 4.20 (d, J=2.1 Hz, 1H), 5.11 (m, 4H), 5.89 (broad s, 1H), 7.23 (m, 4H), 7.32 (m, 6H)

EXAMPLE 4

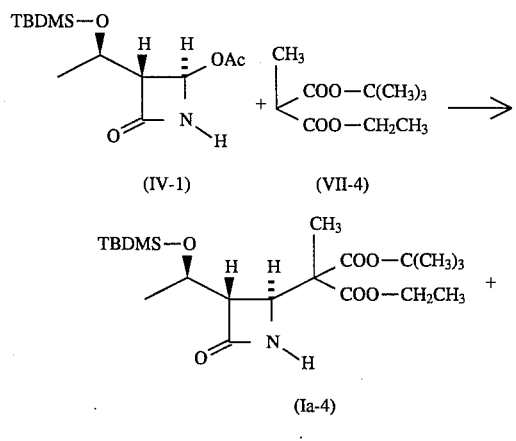

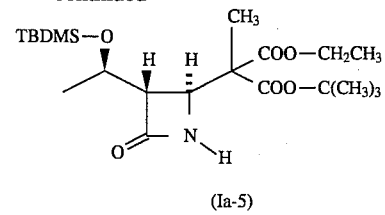

In 15 ml of tetrahydrofuran was suspended 2.17 g (54.3 mmol) of 60% sodium hydride. While this suspension was kept being stirred at room temperature, a solution prepared by dissolving 10.9 g (54.0 mmol) of tert-butyl ethyl methylmalonate (VII-4) in 20 ml of tetrahydrofuran was added thereto dropwise over a period of 1 hour. After the resulting mixture was further stirred at room temperature for 30 minutes, a solution prepared by dissolving 14.1 g (49.1 mmol) of a 4-acetoxyazetidin-2-one derivative (IV-1) in 30 ml of tetrahydrofuran was added thereto dropwise over a period of 20 minutes, and a reaction was allowed to proceed at room temperature overnight.

To the reaction mixture was added 50 ml of a saturated aqueous solution of ammonium chloride. After stirring, extraction was conducted using 50 ml of ethyl acetate. The ethyl acetate layer obtained was washed twice with 25 ml of saturated aqueous common salt solution, subsequently dehydrated with anhydrous magnesium sulfate, and then filtered and concentrated, thereby to obtain a crude product. This crude product was purified by silica gel column chromatography (developing solvent; hexane:ethyl acetate=4:1 by volume), thereby obtaining 14.2 g (percent yield 67%) of an isomer mixture of azetidin-2-one derivatives (Ia-4) and (Ia-5) [isomer ratio (Ia-4):(Ia-5)=77:23 by mol] as white crystals.

Melting point: 73°–74° C. MS (m/e): 414, 372 IR (KBr) cm$^{-1}$: 1765, 1735 $^1$H-NMR (CDCl$_3$) δ ppm: 0.07 (s, 3H), 0.08 (s, 3H), 0.89 (s, 9H), 1.15 (d, J=6.4Hz, 3H×23/100), 1.20 (d, J=6.3 Hz, 3H×77/100), 1.27 (d, J=7.1 Hz, 3H×77/100), 1.29 (d, J=7.1 Hz, 3H×23/100), 1.41 (s, 3H×23/100), 1.42 (s, 3H×77/100), 1.45 (s, 9H×23/100), 1.47 (s, 9H×77/100), 2.98 (m, 1H×23/100), 3.02 (m, 1H×77/100), 4.04 (d, J=2.1Hz, 1H×77/100), 4.09 (d, J=2.2 Hz, 1H×23/100), 4.20 (m, 3H), 5.97 (broad s, 1H)

EXAMPLE 5

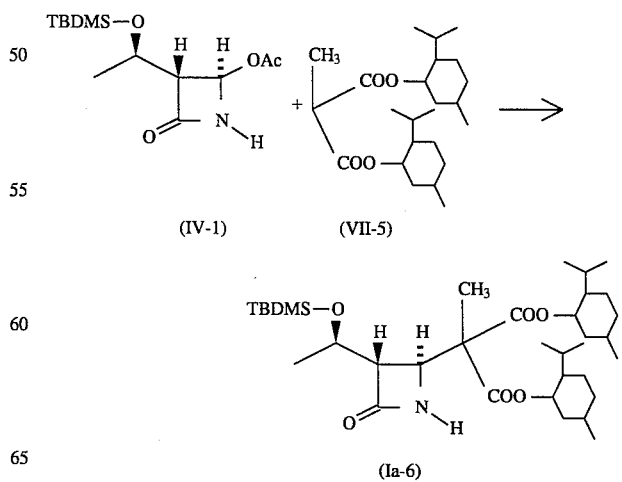

To 0.30 g (7.5 mmol) of 60% sodium hydride was added 3 ml of hexane. This mixture was stirred and the hexane was then removed by decantation. Thereafter, 3.5 ml of tetrahydrofuran was added to the sodium hydride. While the mixture was kept being stirred at room temperature, a solution prepared by dissolving 2.96 g (7.5 mmol) of di-l-menthyl methylmalonate (VII-5) in 5 ml of tetrahydrofuran was added thereto dropwise over a period of 15 minutes. After the resulting mixture was further stirred at room temperature for 30 minutes, a solution prepared by dissolving 2.01 g (7.0 mmol) of a 4-acetoxyazetidin-2-one derivative (IV-1) in 5 ml of tetrahydrofuran was added thereto dropwise over a period of 10 minutes, and a reaction was allowed to proceed at room temperature for 1 hour.

To the reaction mixture was added 10 ml of a saturated aqueous solution of ammonium chloride. After stirring and liquid separation, the tetrahydrofuran layer was washed with saturated aqueous common salt solution and then dehydrated with anhydrous magnesium sulfate. Subsequently, the solvent was removed by distillation to obtain a crude product. This crude product was purified by silica gel column chromatography (developing solvent; hexane:ethyl acetate=8:1 by volume), thereby obtaining 2.94 g (percent yield 68%) of an azetidin-2-one derivative (Ia-6) which was colorless and had an oily consistency.

MS (m/e): 622 ($M^+$+1), 564 IR (neat) $cm^{-1}$: 1770, 1740, 1720 $^1$H-NMR ($CDCl_3$) δ ppm: 0.07 (s, 3H), 0.08 (s, 3H), 0.72 (d, J=7.0 Hz, 3H), 0.77 (d, J=7.0 Hz, 3H), 0.88 (s, 9H), 0.91 (d, J=6.7 Hz, 6H), 0.92 (d, J=6.5 Hz, 6H), 0.95 (m, 6H), 1.22 (d, J=6.3 Hz, 3H), 1.42 (m, 4H), 1.45 (s, 3H), 1.70 (m, 4H), 1.86 (m, 2H), 2.03 (m, 2H), 3.10 (m, 1H), 4.06 (d, J=2.2 Hz, 1H), 4.22 (m, 1H), 4.73 (m, 2H), 5.91 (s, 1H)

EXAMPLE 6

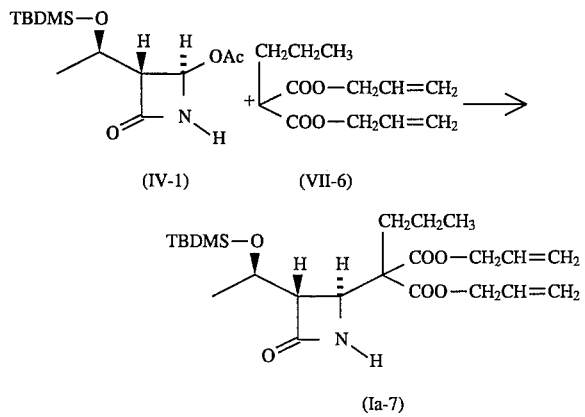

In 50 ml of tetrahydrofuran was suspended 2.92 g (73.0 mmol) of 60% sodium hydride. While this suspension was kept being stirred at room temperature, a solution prepared by dissolving 33.07 g (73.0 mmol) of diallyl n-propylmalonate (VII-6) in 50 ml of tetrahydrofuran was added thereto dropwise. After the resulting mixture was stirred for 2.5 hours, a solution prepared by dissolving 20.10 g (70.0 mmol) of a 4-acetoxyazetidin-2-one derivative (IV-1) in 50 ml of tetrahydrofuran was added thereto dropwise over a period of 30 minutes, and a reaction was allowed to proceed at room temperature for 15 hours.

To the reaction mixture was added 60 ml of a saturated aqueous solution of ammonium chloride. After stirring and liquid separation, the tetrahydrofuran layer obtained was washed with saturated aqueous common salt solution and dehydrated with anhydrous magnesium sulfate. Subsequently, the solvent was removed by distillation to obtain a crude product. This crude product was purified by silica gel column chromatography (developing solvent; hexane:ethyl acetate=10:1 by volume), thereby obtaining 26.32 g (percent yield 83%) of an azetidin-2-one derivative (Ia-7) as white crystals.

Melting point: 47°–48° C. MS (m/e): 438, 396 IR (KBr) $cm^{-1}$: 1770, 1730 $^1$H-NMR ($CDCl_3$) δ ppm: 0.07 (s, 6H), 0.88 (s, 9H), 0.94 (t, J=7.3 Hz, 3H), 1.17 (d, J=6.4 Hz, 3H), 1.25 (m, 1H), 1.47 (m, 1H), 1.80 (ddd, J=4.4, 12.5, 14.0 Hz, 1H), 1.97 (ddd, J=4.6, 12.7, 14.0 Hz, 1H), 3.08 (m, 1H), 4.25 (m, 2H), 4.65 (m, 4H), 5.30 (m, 4H), 5.88 (m, 3H)

EXAMPLE 7

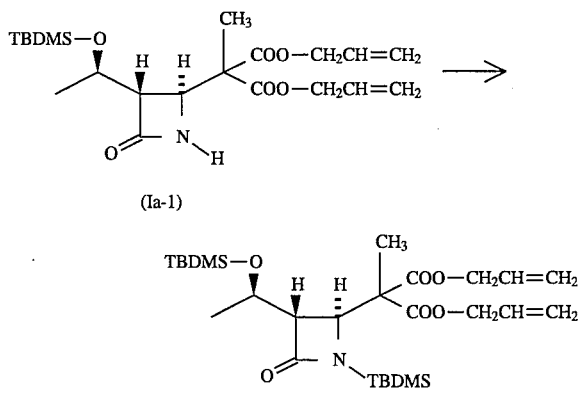

In 20 ml of N,N-dimethylformamide were dissolved 8.50 g (20.0 mmol) of the azetidin-2-one derivative (Ia-1) obtained in Example 1 and 6.04 g (40.0 mmol) of tert-butyldimethylsilyl chloride. To this solution, a solution prepared by dissolving 6.06 g (60.0 mmol) of triethylamine in 5 ml of N,N-dimethylformamide was added dropwise at room temperature over a period of 15 minutes. After the resulting mixture was further stirred for 4 hours, 0.12 g (1.0 mmol) of 4-N,N-dimethylaminopyridine was added thereto, and a reaction was allowed to proceed at room temperature for 6 days.

The reaction mixture was concentrated under a reduced pressure. Thereafter, 40 ml of water was added to the concentrate and extraction was conducted using 200 ml of diethyl ether. The diethyl ether layer obtained was washed with 30 ml of saturated aqueous common salt solution and then dehydrated with anhydrous magnesium sulfate. Subsequently, the solvent was removed by distillation to obtain a crude product. This crude product was purified by alumina column chromatography (developing solvent; hexane:ethyl acetate=from 9:1 to 8:2 by volume), thereby obtaining 8.02 g (percent yield 74%) of an azetidin-2-one derivative (Ib-1) which was colorless and had an oily consistency.

MS (m/e): 540 ($M^+$+1), 524, 482 IR (neat) $cm^{-1}$: 1760, 1740 $^1$H-NMR ($CDCl_3$) δ ppm: 0.07 (s, 3H), 0.08 (s, 3H), 0.11 (s, 3H), 0.29 (s, 3H), 0.89 (s, 9H), 0.96 (s, 9H), 1.22 (d, J=6.2 Hz, 3H), 1.50 (s, 3H), 3.07 (dd, J=2.6, 6.8 Hz, 1H), 4.09 (m, 1H), 4.35 (d, J=2.6 Hz, 1H), 4.64 (m, 4H), 5.30 (m, 4H), 5.90 (m, 2H)

EXAMPLE 8

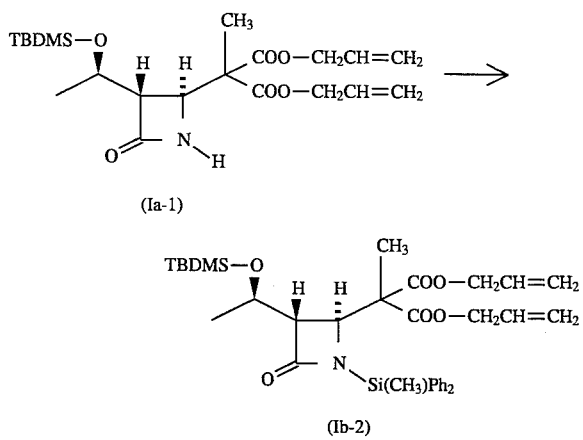

In 13 ml of N,N-dimethylformamide were dissolved 1.70 g (4.0 mmol) of the azetidin-2-one derivative (Ia-1) obtained in Example 1 and 1.12 g (4.8 mmol) of methyldiphenylsilyl chloride. This solution was stirred in an ice bath. Thereto, a solution prepared by dissolving 0.48 g (4.8 mmol) of triethylamine in 2 ml of N,N-dimethylformamide was added dropwise over a period of 40 minutes. The resulting mixture was then allowed to stand overnight in a refrigerator.

From the reaction mixture, the solvent was removed by distillation under a reduced pressure. Subsequently, 10 ml of water and 15 ml of ethyl acetate were added to the residue and extraction was conducted. The ethyl acetate layer obtained was dehydrated with anhydrous magnesium sulfate and the solvent was then removed by distillation, thereby to obtain an oily substance. This oily substance was purified by silica gel column chromatography (developing solvent; hexane:ethyl acetate=5:1 by volume), thereby obtaining 1.69 g (percent yield 68%) of an azetidin-2-one derivative (Ib-2) which was colorless and had an oily consistency.

MS (m/e): 606, 564, 544 IR (neat) cm$^{-1}$: 1755, 1735 $^1$H-NMR (CDCl$_3$) δ ppm: −0.02 (s, 3H), 0.06 (s, 3H), 0.82 (s, 3H), 0.88 (s, 9H), 1.14 (d, J=6.3Hz, 3H), 1.25 (s, 3H), 3.15 (m, 1H), 4.16 (m, 1H), 4.32 (m, 4H), 4.43 (d, J=2.7 Hz, 1H), 5.18 (m, 4H), 5.71 (m, 2H), 7.47 (m, 10H)

EXAMPLE 9

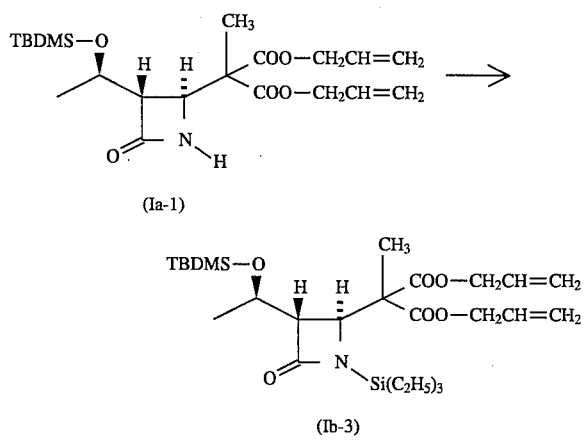

In 25 ml of N,N-dimethylformamide were dissolved 2.87 g (6.7 mmol) of the azetidin-2-one derivative (Ia-1) obtained in Example 1 and 1.58 g (10.5 mmol) of triethylsilyl chloride. This solution was stirred in an ice bath. Thereto, a solution prepared by dissolving 1.06 g (10.5 mmol) of triethylamine in 5 ml of N,N-dimethylformamide was added dropwise over a period of 20 minutes. The resulting mixture was then allowed to stand overnight in a refrigerator.

From the reaction mixture, the solvent was removed by distillation under a reduced pressure. Subsequently, 15 ml of a saturated aqueous solution of sodium hydrogen carbonate and 25 ml of ethyl acetate were added to the residue and extraction was conducted. The ethyl acetate layer obtained was dehydrated with anhydrous magnesium sulfate and the solvent was then removed by distillation, thereby to obtain an oily substance. This oily substance was purified by alumina column chromatography (developing solvent; hexane:ethyl acetate=10:1 by volume), thereby obtaining 2.20 g (percent yield 61%) of an azetidin-2-one derivative (Ib-3) which was colorless and had an oily consistency.

MS (m/e): 524, 511, 482 IR (neat) cm$^{-1}$: 1750 $^1$H-NMR (CDCl$_3$) δ ppm: 0.06 (s, 3H), 0.07 (s, 3H), 0.78 (m, 6H), 0.88 (s, 9H), 0.98 (t, J=7.8 Hz, 9H), 1.26 (d, J=6.3 Hz, 3H), 1.49 (s, 3H), 3.05 (m, 1H), 4.12 (m, 1H), 4.21 (d, J=2.6 Hz, 1H), 4.63 (m, 4H), 5.30 (m, 4H), 5.87 (m, 2H)

EXAMPLE 10

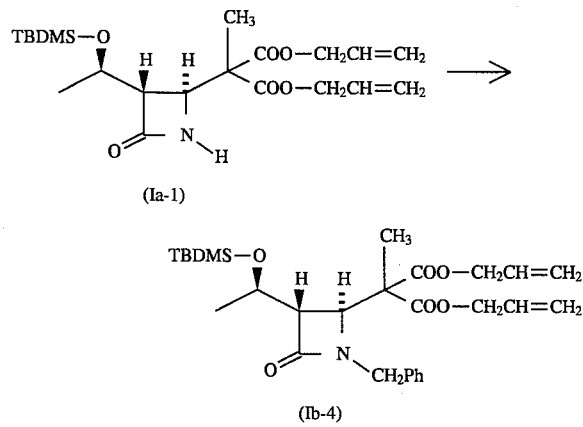

In 5 ml of N,N-dimethylformamide was suspended 0.19 g (4.8 mmol) of 60% sodium hydride. This suspension was cooled to 0° C., and a solution prepared by dissolving 1.93 g (4.5 mmol) of the azetidin-2-one derivative (Ia-1) obtained in Example 1 in 5 ml of N,N-dimethylformamide was added thereto dropwise over a period of 10 minutes. After the resulting mixture was further stirred for 30 minutes, the temperature of the mixture was returned to room temperature. Subsequently, 0.58 g (4.6 mmol) of benzyl chloride was added thereto dropwise and a reaction was allowed to proceed for 4 hours.

To the reaction mixture was added 5 ml of a saturated aqueous solution of ammonium chloride. Extraction was then conducted with 50 ml of diethyl ether. The diethyl ether layer obtained was dehydrated with anhydrous magnesium sulfate and the solvent was then removed by distillation, thereby to obtain a crude product. This crude product was purified by silica gel column chromatography (developing solvent; hexane:ethyl acetate=4:1 by volume), thereby obtaining 1.57 g (percent yield 68%) of an azetidin-2-one derivative (Ib-4) which was colorless and had an oily consistency.

MS (m/e): 516 (M$^+$+1), 500, 458 IR (neat) cm$^{-1}$: 1760, 1740 $^1$H-NMR (CDCl$_3$) δ ppm: −0.01 (s, 3H), 0.05 (s, 3H), 0.85 (s, 9H), 1.13 (d, J=6.3 Hz, 3H), 1.31 (s, 3H), 2.99 (m, 1H), 4.18 (m, 1H), 4.23 (d, J=15.4 Hz, 1H), 4.31 (d, J=2.1Hz, 1H), 4.57 (m, 5H), 5.28 (m, 4H), 5.83 (m, 2H), 7.31 (m, 5H)

EXAMPLE 11

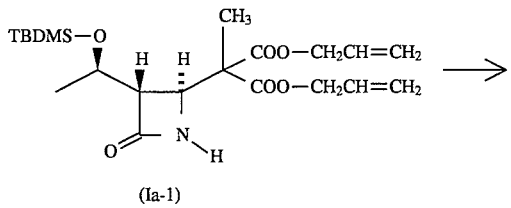
(Ia-1)

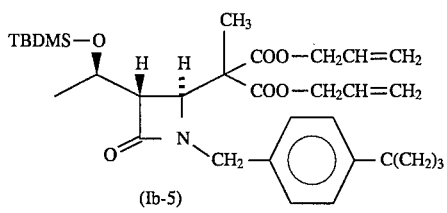
(Ib-5)

Using 2.13 g (5.0 mmol) of the azetidin-2-one derivative (Ia-1) obtained in Example 1, 0.22 g (5.5 mmol) of 60% sodium hydride, and 1.25 g (5.5mmol) of p-tert-butylbenzyl bromide, N-benzylation was conducted in the same manner as in Example 10. Thus, 2.27 g (percent yield 79%) of an azetidin-2-one derivative (Ib-5) was obtained which was colorless and had an oily consistency.

MS (m/e): 556, 514 IR (neat) cm$^{-1}$: 1765, 1740 $^1$H-NMR (CDCl$_3$) δ ppm: −0.06 (s, 3H), 0.03 (s, 3H), 0.84 (s, 9H), 1.13 (d, J=6.3 Hz, 3H), 1.29 (s, 9H), 1.33 (s, 3H), 2.98 (dd, J=2.1, 4.5 Hz, 1H), 4.13 (d, J=15.3 Hz, 1H), 4.14 (m, 1H), 4.35 (d, J=2.1 Hz, 1H), 4.52 (m, 5H), 5.27 (m, 4H), 5.80 (m, 4H), 7.29 (m, 4H)

EXAMPLE 12

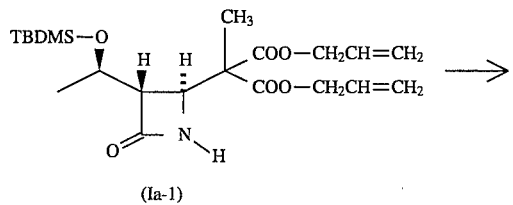
(Ia-1)

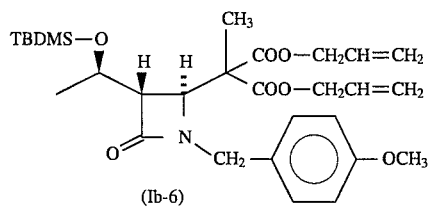
(Ib-6)

Using 2.13 g (5.0 mmol) of the azetidin-2-one derivative (Ia-1) obtained in Example 1, 0.24 g (6.0 mmol) of 60% sodium hydride, and 0.94 g (6.0 mmol) of p-methoxybenzyl chloride, N-benzylation was conducted in the same manner as in Example 10. Thus, 2.07 g (percent yield 76%) of an azetidin-2-one derivative (Ib-6) was obtained which was colorless and had an oily consistency.

MS(m/e): 488 IR (neat) cm$^{-1}$: 1760, 1735 $^1$H-NMR (CDCl$_3$) δ ppm: 0.01 (s, 3H), 0.05 (s, 3H), 0.85 (s, 9H), 1.13 (d, J=6.3 Hz, 3H), 1.30 (s, 3H), 2.98 (dd, J=2.1, 4.3 Hz, 1H), 3.79 (s, 3H), 4.16 (m, 1H), 4.18 (d, J=15.2 Hz, 1H), 4.37 (d, J=2.1Hz, 1H), 4.43 (d, J=15.2 Hz, 1H), 4.59 (m, 4H), 5.28 (m, 4H), 5.82 (m, 2H), 6.83 (dd, J=2.1, 6.3 Hz, 2H), 7.27 (dd, J=2.1, 6.3 Hz, 2H)

EXAMPLE 13

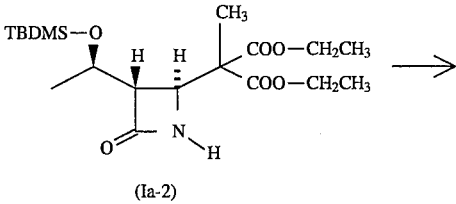
(Ia-2)

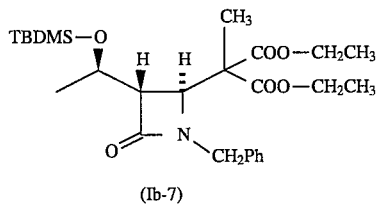
(Ib-7)

Using 4.01 g (10.0 mmol) of the azetidin-2-one derivative (Ia-2) obtained in Example 2, 0.40 g (11.0 mmol) of 60% sodium hydride, and 1.39 g (11.0 mmol) of benzyl chloride, N-benzylation was conducted in the same manner as in Example 10. Thus, 4.30 g (percent yield 88%) of an azetidin-2-one derivative (Ib-7) was obtained which was colorless and had an oily consistency.

MS(m/e): 476, 434 IR (neat) cm$^{-1}$: 1760, 1730 $^1$H-NMR (CDCl$_3$) δ ppm: 0.00 (s, 3H), 0.06 (s, 3H), 0.87 (s, 9H), 1.16 (d, J=6.3 Hz, 3H), 1.20, 1.22 (2 overlapping t, J=7.3 Hz, 6H), 1.30 (s, 3H), 2.99 (dd, J=2.1, 4.5 Hz, 1H), 4.17 (m, 6H), 4.36 (d, J=2.1 Hz, 1H), 4.55 (d, J=15.3 Hz, 1H), 7.31 (m, 5H)

EXAMPLE 14

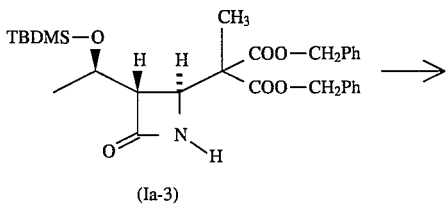
(Ia-3)

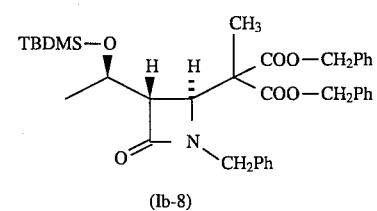
(Ib-8)

To 0.40 g (10.0 mmol) of 60% sodium hydride was added 5 ml of hexane. This mixture was stirred and the hexane was then removed by decantation. To the sodium hydride was added 25 ml of N,N-dimethylformamide. Subsequently, 4.65 g (8.9 mmol) of the azetidin-2-one derivative (Ia-3) obtained in Example 3 was added thereto at room temperature. After the resulting mixture was further stirred at room temperature for 30 minutes, a solution prepared by dissolving 1.12 g (8.9 mmol) of benzyl chloride in 4 ml of N,N-dimethylformamide was added thereto dropwise over a period of 5 minutes, and the mixture was kept being stirred overnight at room temperature.

From the reaction mixture, the solvent was removed by distillation under a reduced pressure. Subsequently, 15 ml of a saturated aqueous solution of sodium hydrogen carbonate and 35 ml of ethyl acetate were added to the residue and extraction was conducted. The ethyl acetate layer obtained was dehydrated with anhydrous magnesium sulfate and the solvent was then removed by distillation, thereby to obtain an oily substance. This oily substance was purified by silica gel column chromatography (developing solvent; hexane:ethyl acetate=2:1 by volume), thereby obtaining 3.50 g (percent yield 64%) of an azetidin-2-one derivative (Ib-8) which was colorless and had an oily consistency.

MS (m/e): 600, 558 IR (neat) cm$^{-1}$: 1760, 1730 $^1$H-NMR (CDCl$_3$) δ ppm: −0.03 (s, 3H), 0.03 (s, 3H), 0.84 (s, 9H), 1.10 (d, J=6.3 Hz, 3H), 1.30 (s, 3H), 3.00 (dd, J=2.1, 4.4 Hz, 1H), 4.12 (d, J=15.4 Hz, 1H), 4.15 (m, 1H), 4.37 (d, J=15.4 Hz, 1H), 4.40 (d, J=2.1 Hz, 1H), 4.94 (d, J=12.2 Hz, 1H), 5.06 (m, 3H), 7.26 (m, 15H)

α-configuration and compound (IIβ-1) in which that methyl group was of the β-configuration were such that α:β=85:15 (by mol). This structure determination was made by separating these isomers by means of high-performance liquid chromatography (HPLC) (column; Inertsil ODS, manufactured by GL Sciences Inc., Japan, developing solvent; acetonitrile:water:acetic acid=700:300:3 by volume).

α Isomer (IIα-1)

Melting point: 168°–170° C. MS (m/e): 286, 244 IR (KBr) cm$^{-1}$: 1720 $^1$H-NMR (CDCl$_3$) δ ppm: 0.07 (s, 3H), 0.08 (s, 3H), 0.88 (s, 9H), 1.25 (2 overlapping d, J=6.2, 7.3 Hz, 6H), 2.56 (qd, J=7.3, 9.8 Hz, 1H), 2.80 (dd, J=2.0, 5.3 Hz, 1H), 3.70 (dd, J=2.0, 9.8 Hz, 1H), 4.19 (m, 1H), 6.67 (broad s, 1H)

β Isomer (IIβ-1)

Melting point: 143.5°–144.5° C. MS (m/e): 286, 244 IR (KBr) cm$^{-1}$: 1720 $^1$H-NMR (CDCl$_3$) δ ppm: 0.07 (s, 3H), 0.08 (s, 3H), 0.87 (s, 9H), 1.20 (d, J=6.3 Hz, 3H), 1.27 (d, J=7.0 Hz, 3H), 2.75 (qd, J=5.0, 7.0 Hz, 1H), 3.03 (dd, J=2.2, 4.3 Hz, 1H), 3.94 (dd, J=2.2, 5.0 Hz, 1H), 4.20 (qd, J=4.5, 6.3 Hz, 1H), 6.25 (broad s, 1H)

EXAMPLE 15

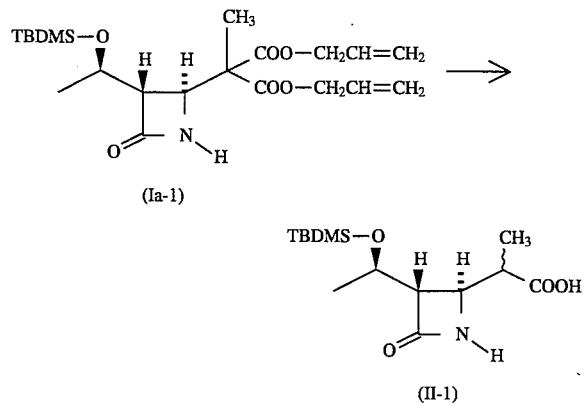

EXAMPLE 16

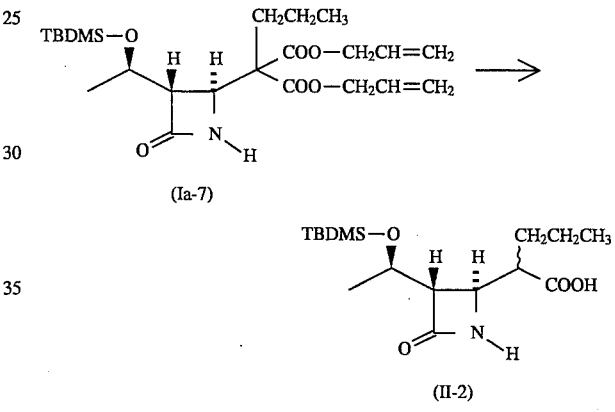

In an argon stream, 4.8 mg (0.02 mmol) of palladium acetate was suspended in 2 ml of 1,4-dioxane, and a solution prepared by dissolving 52.0 mg (0.2 mmol) of triphenylphosphine in 2 ml of 1,4-dioxane was added dropwise to the suspension. Subsequently, the resulting mixture was heated with refluxing and, further, a solution prepared by dissolving 0.85 g (2.0 mmol) of the azetidin-2-one derivative (Ia-1) obtained in Example 1, 0.37 g (7.9 mmol) of formic acid, and 0.81 g (8.0 mmol) of triethylamine in 6 ml of 1,4-dioxane was added thereto dropwise. A reaction was then allowed to proceed for 3 hours.

To the reaction mixture were added 10 ml of a 5% aqueous solution of sodium hydroxide and 10 ml of ethyl acetate. After liquid separation, the aqueous layer was acidified with 1N hydrochloric acid and extraction was then conducted with 20 ml of ethyl acetate. The ethyl acetate layer obtained was dehydrated with anhydrous magnesium sulfate and the solvent was then removed by distillation, thereby obtaining 0.47 g (percent yield 78%) of the desired compound, a 4-(1-carboxyethyl)-azetidin-2-one derivative (II-1), as white crystals.

In the compound (II-1) thus obtained, the proportions of compound (IIα-1) in which the methyl group at the wavy line in the formula showing the compound (II-1) was of the In a nitrogen atmosphere, a solution prepared by dissolving 746.0 mg (16.22 mmol) of formic acid and 1,647.7 mg (16.31 mmol) of triethylamine in 10 ml of 1,4-dioxane was added to a solution prepared by dissolving 9.0 mg (0.04 mmol) of palladium acetate and 53.0 mg (0.20 mmol) of triphenylphosphine in 8 ml of 1,4-dioxane, and this mixture was heated with refluxing. Thereto was added dropwise, over a period of 40 minutes, a solution prepared by dissolving 1,815.4 mg (4.01 mmol) of the azetidin-2-one derivative (Ia-7) obtained in Example 6 in 5 ml of 1,4-dioxane. The resulting mixture was kept being heated with refluxing for further 5 hours.

The reaction mixture was cooled to room temperature, and extraction was conducted with 15 ml of diethyl ether and 20 ml of a 5% aqueous solution of sodium hydroxide. Subsequently, 2N hydrochloric acid was added to the alkaline layer to adjust it to pH 2, and extraction was conducted with two 35 ml portions of ethyl acetate. The ethyl acetate layer obtained was washed with saturated aqueous common salt solution, subsequently dehydrated with anhydrous magnesium sulfate, and then filtered and concentrated, thereby obtaining 985.8 mg (percent yield 75%) of the desired compound, a 4-(1-carboxybutyl)azetidin-2-one derivative (II-2), as white crystals.

In the compound (II-2) thus obtained, the proportions of compound (IIα-2) in which the n-propyl group at the wavy line in the formula showing the compound (II-2) was of the α-configuration and compound (IIβ-2) in which that n-propyl group was of the β-configuration were such that α:β= 73:27 (by mol). This structure determination was made by separating these isomers by means of HPLC (conditions concerning the column and developing solvent were the same as those in Example 15).

α Isomer (IIα-2)

Melting point: 173°–174° C. MS (m/e): 314, 272 IR (KBr) cm$^{-1}$: 1720 $^1$H-NMR (CD$_3$OD) δ ppm: 0.08 (s, 3H), 0.10 (s, 3H), 0.90 (s, 9H), 0.94 (t, J=7.2 Hz, 3H), 1.23 (d, J=6.3 Hz, 3H), 1.40 (m, 2H), 1.60 (m, 2H), 2.47 (m, 1H), 2.88 (dd, J=2.0, 4.3 Hz, 1H), 3.78 (dd, J=2.0, 8.7 Hz, 1H), 4.20 (qd, J=4.3, 6.3 Hz, 1H)

β Isomer (IIβ-2)

Melting point: 164.5°–166° C. MS (m/e): 314, 272 IR (KBr) cm$^{-1}$: 1720 $^1$H-NMR (CD$_3$OD) δ ppm: 0.07 (s, 3H), 0.08 (s, 3H), 0.89 (s, 9H), 0.95 (t, J=7.2 Hz, 3H), 1.16 (d, J=6.4 Hz, 3H), 1.45 (m, 3H), 1.64 (m, 1H), 2.48 (m, 1H), 3.01 (dd, J=2.0, 2.7 Hz, 1H), 3.77 (dd, J=2.0, 8.4 Hz, 1H), 4.22 (qd, J=2.7, 6.4 Hz, 1H)

EXAMPLE 17

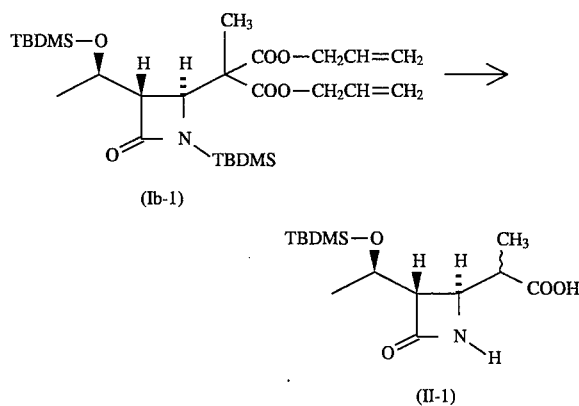

In a nitrogen atmosphere, 0.56 g (12.0 mmol) of formic acid was added to a solution prepared by dissolving 4.5 mg (0.02 mmol) of palladium acetate and 10.5 mg (0.04 mmol) of triphenylphosphine in 2.5 ml of toluene, and this mixture was stirred with heating at 70° C. To this reaction mixture was added dropwise, over a period of 15 minutes, a solution prepared by dissolving 0.54 g (1.0 mmol) of the azetidin-2-one derivative (Ib-1) obtained in Example 7 in 2 ml of toluene. The mixture was then kept being further stirred at 70° C. for 3.5 hours.

The reaction mixture was cooled to room temperature and 15 ml of diethyl ether and 5 ml of 2N hydrochloric acid were added thereto. After the resulting mixture was stirred for 20 minutes, liquid separation was conducted. The diethyl ether layer was extracted with three 10 ml portions of a 5% aqueous solution of sodium hydroxide. Thereafter, 2N hydrochloric acid was added to the aqueous layer to adjust it to pH 2 and extraction was conducted with two 20 ml portions of diethyl ether. The diethyl ether layer obtained was washed with saturated aqueous common salt solution, subsequently dehydrated with anhydrous magnesium sulfate, and then filtered and concentrated, thereby obtaining 0.23 g (percent yield 76%) of the desired compound (II-1).

In the compound (II-1) thus obtained, the proportions of isomers were such that (IIα-1):(IIβ-1)=6:94 (by mol).

EXAMPLE 18

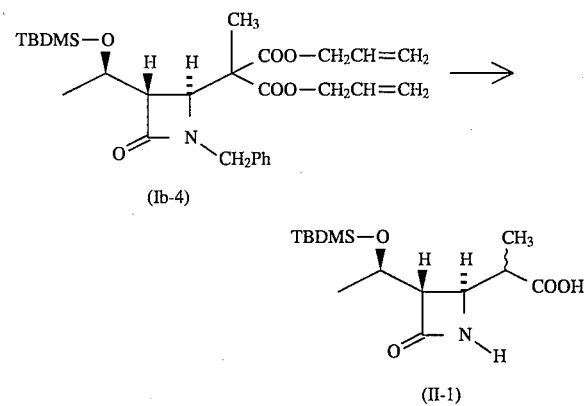

In a nitrogen atmosphere, a solution prepared by dissolving 2.02 g (44.0 mmol) of formic acid and 5.55 g (55.0 mmol) of triethylamine in 15 ml of tetrahydrofuran was added to a solution prepared by dissolving 24.8 mg (1.1 mmol) of palladium acetate and 57.6 mg (2.2 mmol) of triphenylphosphine in 15 ml of tetrahydrofuran, and this mixture was heated with refluxing. To this reaction mixture was added dropwise, over a period of 30 minutes, a solution prepared by dissolving 5.68 g (11.0 mmol) of the azetidin-2-one derivative (Ib-4) obtained in Example 10 in 20 ml of tetrahydrofuran. The resulting mixture was kept being stirred for further 1.5 hours.

The reaction mixture was cooled to room temperature and 80 ml of diethyl ether was added thereto. After liquid separation, the mixture was washed with 30 ml of saturated aqueous common salt solution and dehydrated with anhydrous magnesium sulfate. The solvent was then removed by distillation under a reduced pressure thereby to obtain 4.41 g of a crude product.

Subsequently, 1.29 g (56.0 mmol) of sodium metal was added to 100 ml of liquid ammonia cooled to −60° C. Immediately after the sodium had dissolved and the liquid had turned dark blue, a solution prepared by dissolving 4.41 g of the crude product obtained above in 20 ml of diethyl ether was added thereto dropwise over a period of 30 minutes. Cooling of the reactor was stopped, and the temperature of the reaction mixture was returned to room temperature over a period of one night while the reaction mixture was kept being stirred. To the resulting reaction mixture were added 50 ml of diethyl ether and 50 ml of water. This mixture was stirred and liquid separation was then conducted. To the aqueous layer obtained, an extract was added which had been obtained by extracting the diethyl ether layer with 20 ml of a 5% aqueous solution of sodium hydroxide. Subsequently, the resulting mixture was adjusted to pH 2 with diluted hydrochloric acid. This mixture was extracted with 100 ml of diethyl ether, and the extract was washed with 30 ml of saturated aqueous common salt solution, subsequently dehydrated with anhydrous magnesium sulfate, and then filtered and concentrated, thereby obtaining 2.60 g (percent yield 77%) of the desired compound (II-1).

In the compound (II-1) thus obtained, the proportions of isomers were such that (IIα-1):(IIβ-1)=31:69 (by mol).

EXAMPLE 19

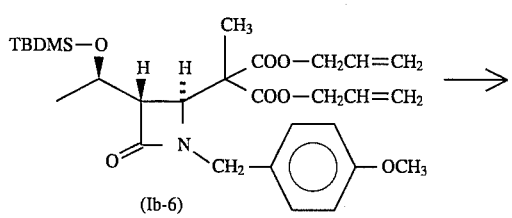

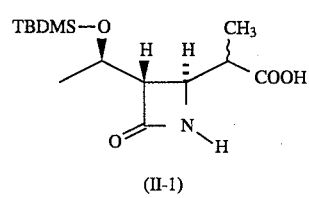

Using 1.09 g (2.0 mmol) of the azetidin-2-one derivative (Ib-6) obtained in Example 12, 9.0 mg (0.04 mmol) of palladium acetate, 21.0 mg (0.08 mmol) of triphenylphosphine, 0.37 g (8.0 mmol) of formic acid, and 0.91 g (9.0 mmol) of triethylamine, de-esterification and decarboxylation reactions were conducted in the same manner as in Example 18. Subsequently, debenzylation reaction was performed using 30 ml of liquid ammonia and 0.24 g (10.0 mmol) of sodium metal. Thus, 0.48 g (percent yield 80%) of the desired compound (II-1) was obtained.

In the compound (II-1) thus obtained, the proportions of isomers were such that (IIα-1):(IIβ-1)=39:61 (by mol).

EXAMPLE 20

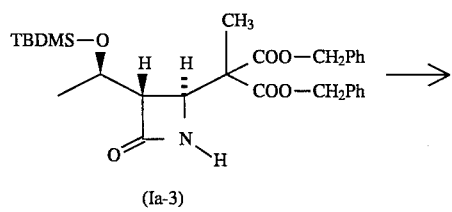

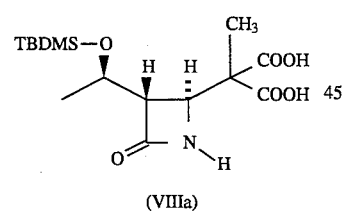

In 30 ml of methanol were suspended 1.58 g (3.0 mmol) of the azetidin-2-one derivative (Ia-3) obtained in Example 3, 0.72 g (7.1 mmol) of triethylamine, and 0.3 g of 5% palladium carbon. Hydrogenation was then conducted at ordinary pressure.

The palladium carbon was removed from the resulting reaction mixture by filtration. Thereafter, the methanol was removed by distillation under a reduced pressure, and 10 ml of a saturated aqueous solution of sodium hydrogen carbonate and 10 ml of ethyl acetate were added to the residue. This mixture was stirred and liquid separation was conducted. The aqueous layer was acidified with 1N hydrochloric acid and the white solid thus formed was filtered off, washed with water, and then dried under a reduced pressure, thereby obtaining 0.54 g (percent yield 52%) of a dicarboxylic acid compound (VIIIa).

Melting point: 110°–111° C. MS (m/e): 244, 200 IR (KBr) cm$^{-1}$: 1755, 1720 $^1$H-NMR (CD$_3$OD) δ ppm: 0.02 (s, 3H), 0.04 (s, 3H), 0.86 (s, 9H), 1.13 (d, J=6.4 Hz, 3H), 1.33 (s, 3H), 3.01 (dd, J=2.1, 2.7 Hz, 1H), 4.19 (d, J=2.1 Hz, 1H), 4.20 (m, 1H)

EXAMPLE 21

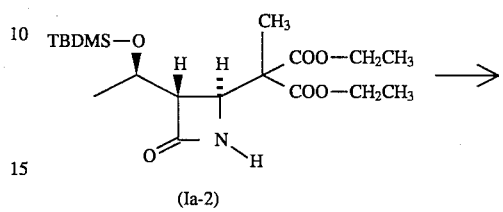

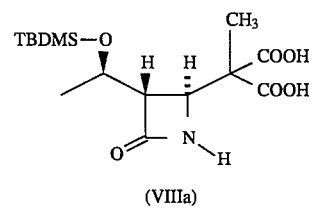

In a mixture of 15 ml of ethanol and 5 ml of water was dissolved 1.08 g (2.7 mmol) of the azetidin-2-one derivative (Ia-2) obtained in Example 2. Thereto was added a solution prepared by dissolving 0.99 g (17.6 mmol) of potassium hydroxide in 3 ml of water. This mixture was kept being stirred for 5 hours with heating at 50° C.

The reaction mixture was cooled to room temperature and then poured into 30 ml of water. The resulting mixture was acidified with 2N hydrochloric acid and the white solid thus formed was filtered off, washed with water, and then dried under a reduced pressure, thereby obtaining 0.63 g (percent yield 68%) of a dicarboxylic acid compound (VIIIa).

EXAMPLE 22

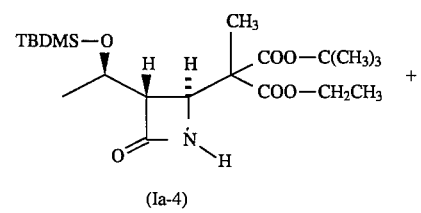

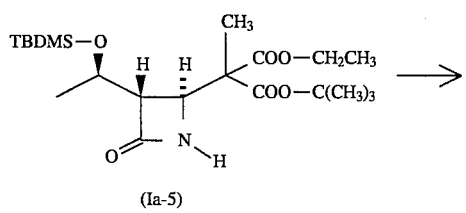

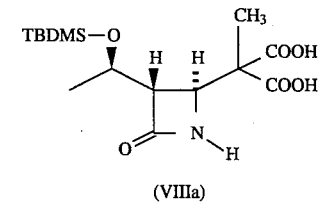

In 2 ml of ethanol was dissolved 0.40 g (0.93 mmol) of the isomer mixture consisting of azetidin-2-one derivatives (Ia-4) and (Ia-5) obtained in Example 4. Thereto was added a solution prepared by dissolving 0.34 g (6.1 mmol) of potassium hydroxide in 3 ml of water. This mixture was kept being stirred at 50° C. for 2 days.

The reaction mixture was concentrated under a reduced pressure and 1N hydrochloric acid was then added thereto to adjust it to pH 2. Thereafter, the resulting mixture was further concentrated under a reduced pressure. To the solid thus obtained, 10 ml of diethyl ether was added. This mixture was stirred sufficiently and then filtered and concentrated, thereby obtaining 0.21 g (percent yield 66%) of a dicarboxylic acid compound (VIIIa).

EXAMPLE 23

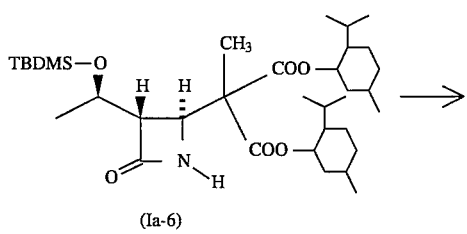
(Ia-6)

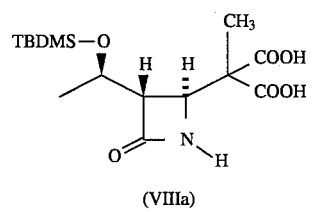
(VIIIa)

In a mixture of 10 ml of ethanol and 3 ml of water was dissolved 0.62 g (1.0 mmol) of the azetidin-2-one derivative (Ia-6) obtained in Example 5. Thereto was added a solution prepared by dissolving 0.38 g (6.8 mmol) of potassium hydroxide in 3 ml of water. This mixture was kept being stirred at 50° C. for 25 hours.

The reaction mixture was cooled to room temperature and then poured into 30 ml of water. Extraction was conducted with two 10 ml portions of diethyl ether. The aqueous layer obtained was acidified with 2N hydrochloric acid and extraction was conducted with two 15 ml portions of ethyl acetate. Subsequently, the extract was dehydrated with anhydrous magnesium sulfate and then filtered and dried under a reduced pressure, thereby obtaining 0.18 g (percent yield 52%) of a dicarboxylic acid compound (VIIIa).

EXAMPLE 24

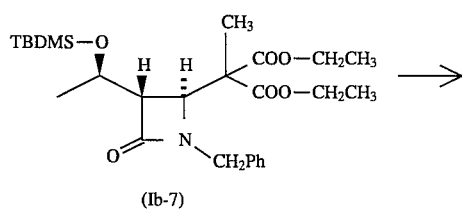
(Ib-7)

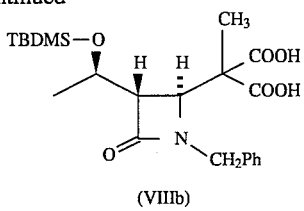
(VIIIb)

To 2.40 g (4.9 mmol) of the azetidin-2-one derivative (Ib-7) obtained in Example 13 were added 5 ml of ethanol and 10 ml of water. Thereto was added, with stirring, a solution prepared by dissolving 1.10 g (19.6 mmol) of potassium hydroxide in 5 ml of water. This mixture was stirred overnight at room temperature.

The resulting reaction mixture was poured into 50 ml of water and 1N hydrochloric acid was added thereto to adjust it to pH 7. Extraction was then conducted using 50 ml of diethyl ether. Thereafter, 1N hydrochloric acid was added to the extract until it became pH 1, and 50 ml of diethyl ether was then added thereto to conduct extraction. The diethyl ether layer obtained was washed with 15 ml of saturated aqueous common salt solution, subsequently dehydrated with anhydrous magnesium sulfate, and then filtered and concentrated, thereby obtaining 1.50 g (percent yield 69%) of a dicarboxylic acid compound (VIIIb).

Melting point: 128°–129° C. MS (m/e): 334, 290 IR (KBr) cm$^{-1}$: 1750, 1730 $^1$H-NMR (CD$_3$OD) δ ppm: 0.01 (s, 3H), 0.07 (s, 3H), 0.86 (s, 9H), 1.16 (d, J=6.4 Hz, 3H), 1.21 (s, 3H), 3.04 (m, 1H), 4.21 (m, 1H), 4.30 (d, J=15.2 Hz, 1H), 4.45 (d, J=2.1 Hz, 1H), 4.46 (d, J=15.2 Hz, 1H), 7.30 (m, 5H)

EXAMPLE 25

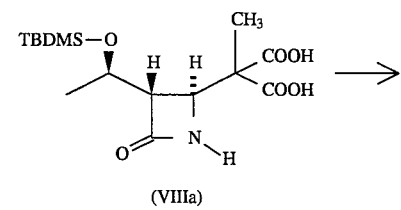
(VIIIa)

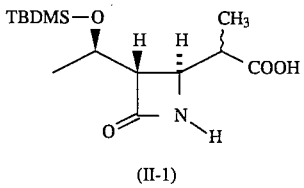
(II-1)

In 15 ml of diethylene glycol dimethyl ether was dissolved 1.38 g (4.0 mmol) of the dicarboxylic acid compound (VIIIa) obtained in Examples 20 to 23. This solution was heated at 120° C. for 3 hours.

The reaction mixture was cooled to room temperature and extraction was then conducted using 20 ml of diethyl ether and 15 ml of a 5% aqueous solution of sodium hydroxide. Thereafter, the aqueous layer was washed with 10 ml of diethyl ether and then adjusted to pH 2 with 2N hydrochloric acid, and extraction was conducted using 30 ml of diethyl ether. The diethyl ether layer obtained was washed with 10 ml of saturated aqueous common salt solution, subsequently dehydrated with anhydrous magnesium sulfate, and then filtered and concentrated, thereby obtaining 0.97 g (percent yield 80%) of the desired compound (II-1).

In the compound (II-1) thus obtained, the proportions of isomers were such that (IIα-1):(IIβ-1)=90:10 (by mol).

EXAMPLE 26

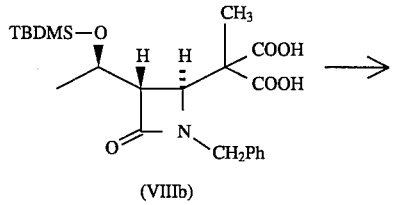

(VIIIb)

→

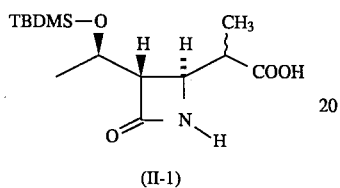

(II-1)

In the same manner as in Example 23, 0.87 g (2.0 mmol) of the dicarboxylic acid compound (VIIIb) obtained in Example 24 was heated to conduct decarboxylation reaction. Thereafter, debenzylation reaction was performed using liquid ammonia and sodium metal in the same manner as in Example 18, thereby obtaining 0.42 g (percent yield 70%) of the desired compound (II-1).

In the compound (II-1) thus obtained, the proportions of isomers were such that (IIα-1):(IIβ-1)=28:72 (by mol).

While the invention has been described in detail and with reference to specific embodiments thereof, it will be apparent to one skilled in the art that various changes and modifications can be made therein without departing from the spirit and scope thereof.

What is claimed is:

1. A process for preferentially producing a 4-(1-carboxyalkyl)azetidin-2-one derivative represented by formula (IIβ):

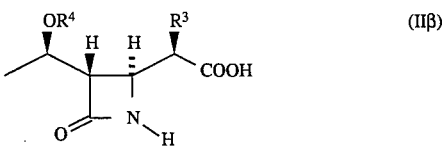

wherein $R^3$ represents a lower alkyl group and $R^4$ represents a hydrogen atom or a hydroxy-protective group, which comprises deesterifying and decarboxylating a 4-(1,1-dialkoxycarbonylalkyl) azetidin-2-one derivative represented by formula (I):

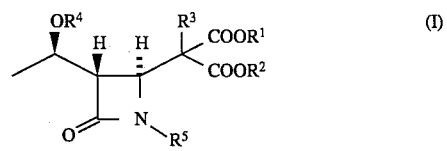

wherein $R^1$ and $R^2$ are identical or different and each represents an alkyl group, an alkenyl group, or an aralkyl group, $R^3$ and $R^4$ each has the meaning as defined above, and $R^5$ represents an amino-protective group, and after that, eliminating the amino-protective group from the derivative; wherein said 4-(1-carboxyalkyl)azetidin-2-one derivative of formula (IIβ) is present in an amount of at least 61% by mol of all 4-(1-carboxyalkyl)azetidin-2-one derivatives produced.

2. The process as claimed in claim 1, wherein $R^1$ and $R^2$ in formula (I) each is a 2-alkenyl group and the deesterification and decarboxylation reactions are conducted by reacting formic acid or an amine salt of formic acid with the azetidin-2-one derivative of formula (I) in the presence of a palladium compound which generates zerovalent palladium in the reaction system.

\* \* \* \* \*